(12) United States Patent
Ishikawa (10) Patent No.: US 11,311,697 B2
(45) Date of Patent: Apr. 26, 2022

(54) CATHETER

(71) Applicant: ASAHI INTECC CO., LTD., Seto (JP)

(72) Inventor: Masatomo Ishikawa, Seto (JP)

(73) Assignee: ASAHI INTECC CO., LTD., Seto (JP)

( * ) Notice: Subject to any disclaimer, the term of this patent is extended or adjusted under 35 U.S.C. 154(b) by 318 days.

(21) Appl. No.: 16/729,535

(22) Filed: Dec. 30, 2019

(65) Prior Publication Data

US 2020/0129730 A1    Apr. 30, 2020

Related U.S. Application Data

(63) Continuation of application No. PCT/JP2017/024185, filed on Jun. 30, 2017.

(51) Int. Cl.
| | |
|---|---|
| *A61M 25/00* | (2006.01) |
| *A61L 29/08* | (2006.01) |
| *A61M 25/09* | (2006.01) |

(52) U.S. Cl.
CPC ......... *A61M 25/005* (2013.01); *A61L 29/085* (2013.01); *A61M 25/0012* (2013.01); *A61M 25/0053* (2013.01); *A61M 2025/09083* (2013.01); *A61M 2025/09091* (2013.01)

(58) Field of Classification Search
CPC ............ A61M 25/005; A61M 25/0012; A61M 25/00; A61M 25/0068; A61M 25/0045; A61M 25/0054; A61M 25/0053; A61M 2025/09091; A61M 2025/09083
See application file for complete search history.

(56) References Cited

U.S. PATENT DOCUMENTS

| | | | |
|---|---|---|---|
| 5,507,766 A | 4/1996 | Kugo et al. | |
| 2004/0064130 A1 * | 4/2004 | Carter | A61M 25/0009 604/523 |
| 2009/0018525 A1 * | 1/2009 | Waite | A61M 25/0068 604/508 |
| 2010/0318065 A1 | 12/2010 | Miyata et al. | |
| 2011/0245775 A1 * | 10/2011 | Tekulve | A61M 25/0662 604/171 |
| 2012/0089127 A1 | 4/2012 | Miyata et al. | |

(Continued)

FOREIGN PATENT DOCUMENTS

| | | |
|---|---|---|
| CN | 102430184 A | 5/2012 |
| CN | 105879191 A | 8/2016 |

(Continued)

*Primary Examiner* — Nathan R Price
*Assistant Examiner* — Anh Bui
(74) *Attorney, Agent, or Firm* — Xsensus LLP (57) ABSTRACT

A catheter that includes a tubular inner layer, a first reinforcing body that is wound around an outside in a radial direction of the inner layer, a second reinforcing body that is wound around the outside in the radial direction of the first reinforcing body, and an outer layer that covers the inner layer, the first reinforcing body, and the second reinforcing body, and the inner layer has a reduced diameter portion that is reduced in diameter from a proximal end side of the catheter toward a distal end side of the catheter on an inner peripheral surface of the inner layer, and a thickness of the outer layer between the first reinforcing body and the second reinforcing body is increased, at least partially from the proximal end side toward the distal end side, in the radial direction of the reduced diameter portion.

14 Claims, 4 Drawing Sheets

(56) References Cited

U.S. PATENT DOCUMENTS

| | | | |
|---|---|---|---|
| 2012/0179141 A1 | 7/2012 | Miyata et al. | |
| 2012/0310213 A1* | 12/2012 | Kronfeld | A61M 25/001 604/526 |
| 2016/0235941 A1* | 8/2016 | Matsumoto | A61M 25/0026 |

FOREIGN PATENT DOCUMENTS

| | | | |
|---|---|---|---|
| JP | 06-277296 | A | 10/1994 |
| JP | 09-512445 | A | 12/1997 |
| JP | 2004-512150 | A | 4/2004 |
| JP | 2008-229160 | A | 10/2008 |
| JP | 2016-152907 | A | 8/2016 |
| WO | 1995/28982 | A1 | 11/1995 |
| WO | 2002/36194 | A2 | 5/2002 |

\* cited by examiner

CATHETER

CROSS REFERENCES TO RELATED APPLICATIONS

This application is a continuation of International Application No. PCT/JP2017/024185, filed Jun. 30, 2017.

TECHNICAL FIELD

The present disclosure relates to a medical catheter.

BACKGROUND

Conventionally, there is known a catheter including a first reinforcing body and a second reinforcing body for the purpose of preventing deformation of the shape of a lumen, exerting rotational torque when entering a blood vessel, and the like. An example of such a catheter is described in the following patent literatures.

CITATION LIST

Patent Literature

Patent Literature 1: Japanese Patent Application Laid-open No. 2008-229160
Patent Literature 2: Japanese Patent Application Laid-open No. 2016-152907

SUMMARY

The present application provides a catheter, comprising: a tubular inner layer; a first reinforcing body that is wound around an outside in a radial direction of the inner layer; a second reinforcing body that is wound around the outside in the radial direction of the first reinforcing body; and an outer layer that covers the inner layer, the first reinforcing body, and the second reinforcing body, wherein the inner layer has a reduced diameter portion that is reduced in diameter from a proximal end side of the catheter toward a distal end side of the catheter on an inner peripheral surface of the inner layer, and a thickness of the outer layer between the first reinforcing body and the second reinforcing body is increased, at least partially from the proximal end side toward the distal end side, in the radial direction of the reduced diameter portion.

DETAILED DESCRIPTION

Technical Problem

In addition, there exists a catheter having, on the inner peripheral surface thereof, a reduced-diameter portion that is reduced in diameter from the proximal end side toward the distal end side. In the catheter having such a reduced diameter portion, a guide wire inserted into the catheter contacts the inner peripheral surface of the reduced diameter portion. For this reason, it is desirable to ensure the flexibility of the reduced diameter portion. However, it is difficult to ensure the flexibility of the reduced diameter portion in a catheter including two reinforcing bodies, the first reinforcing body and the second reinforcing body.

In view of the above-described aspect, the present disclosure aims at providing a catheter including a first reinforcing body and a second reinforcing body that is capable of ensuring the flexibility of a reduced diameter portion.

Solution to Problem

To achieve the above-described object, the present specification discloses a catheter including a tubular inner layer, a first reinforcing body that is wound around the outside in the radial direction of the inner layer, a second reinforcing body that is wound around the outside in the radial direction of the first reinforcing body, and an outer layer that covers the inner layer, the first reinforcing body, and the second reinforcing body, in which the inner layer has a reduced diameter portion that is reduced in diameter from the proximal end side toward the distal end side on the inner peripheral surface, and the thickness of the outer layer between the first reinforcing body and the second reinforcing body is increased, at least partially from the proximal end side toward the distal end side, in the radial direction of the reduced diameter portion.

Advantageous Effects of Disclosure

According to the present disclosure, the thickness of the outer layer between the first reinforcing body and the second reinforcing body is increased at least partially from the proximal end side toward the distal end side in the radial direction of the reduced diameter portion. Therefore, in the radial direction of the reduced diameter portion, the layer between the first reinforcing body and the second reinforcing body functions as a cushion, and it is possible to ensure the flexibility of the reduced diameter portion.

First Embodiment

Hereinafter, a catheter according to an embodiment of the present disclosure will be described with reference to the enclosed drawings.

Figure 1:
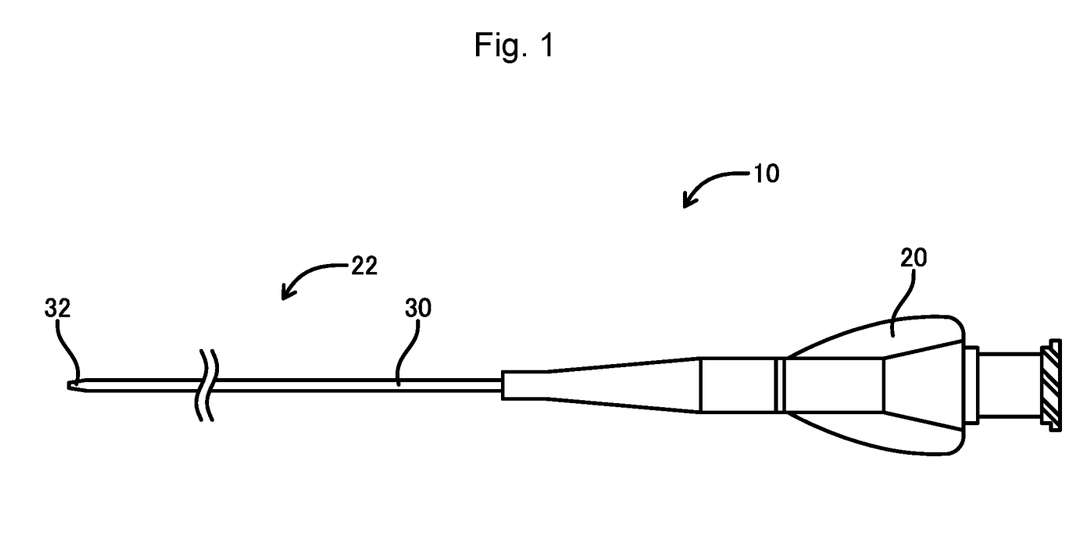
FIG. 1 is a plan view of a catheter according to a first embodiment.
Figure 2:
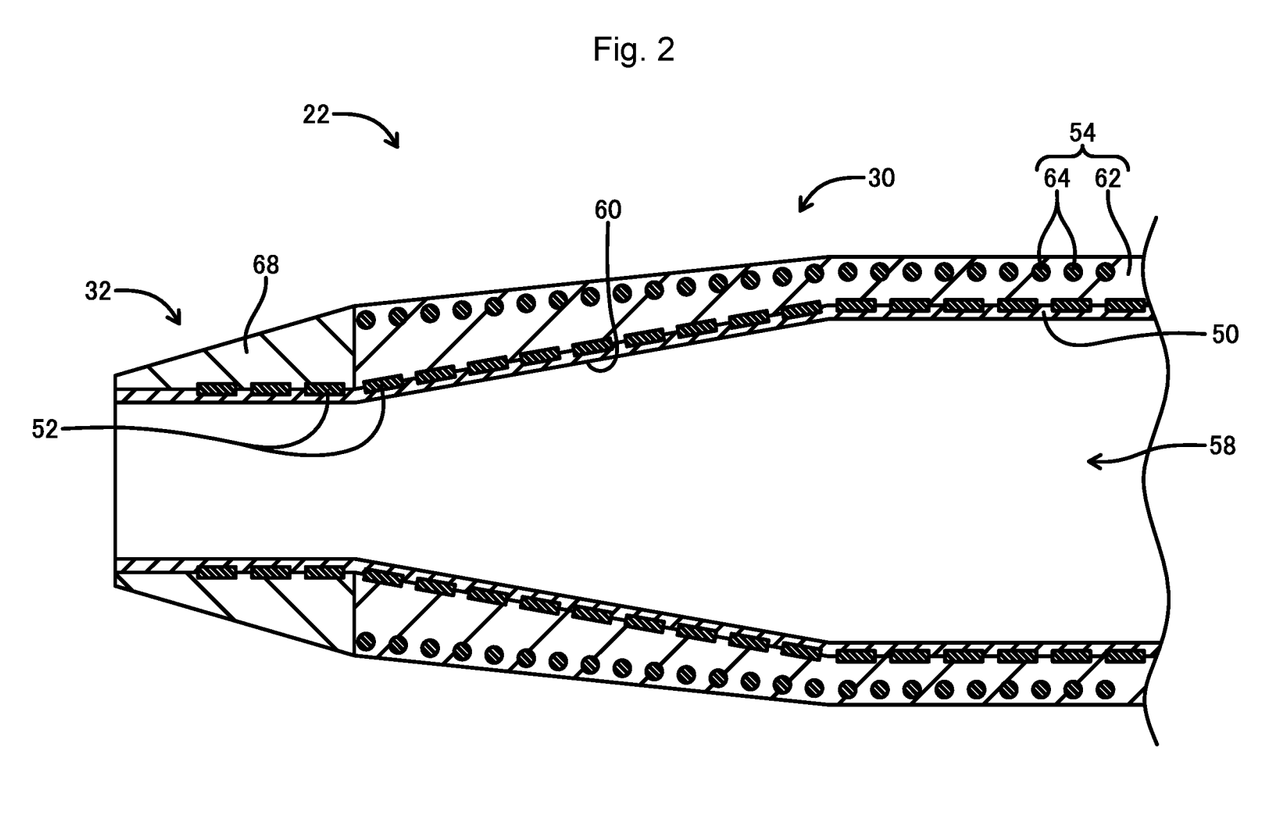
FIG. 2 is a partially enlarged sectional view of the catheter according to the first embodiment.

FIG. 1 is a plan view of a catheter according to the first embodiment of the present disclosure, and FIG. 2 is a partially enlarged sectional view of the catheter according to the first embodiment.

As illustrated in FIG. 1, the catheter 10 includes an operation part 20 operated by an operator, and a catheter tube 22 connected to the distal end of the operation part 20. Note that the side connected to the operation part 20 of the catheter tube 22 is described as a proximal end side, and the opposite side to the proximal end side is described as a distal end side.

The catheter tube 22 has a tubular shape and includes a catheter main body 30 extending from the operation part 20 and a distal tip 32 positioned on the distal end side of the catheter main body 30. In the catheter 10, a guide wire (not illustrated) is inserted from the end on the proximal end side of the catheter main body 30 via the operation part 20 and extends from the end on the distal end side of the distal tip 32.

As illustrated in FIG. 2, the catheter main body 30 has a multilayer structure, and includes an inner layer 50, a braid 52 corresponding to the first reinforcing body, and a reinforcing layer 54 in this order from the radially inner side with respect to the central axis of the catheter main body 30. Note that the radial direction is a direction extending radially from the central axis of the tubular member.

The inner layer 50 has a tubular shape having a lumen 58 and is disposed across the catheter main body 30 and the distal tip 32. The inner layer 50 has a reduced diameter portion 60 that is reduced in diameter from the proximal end side toward the distal end side on the inner peripheral surface. The reduced diameter portion 60 extends from a part between the end on the proximal end side of the catheter main body 30 and the end on the distal end side thereof to the end on the distal end side of the catheter main body 30. Moreover, in the inner layer 50, the film thickness is substantially uniform over the entire area. Thus, the outer peripheral surface of the inner layer 50 is also reduced in diameter in the same manner as the inner peripheral surface. That is, in the reduced diameter portion 60, the inner layer 50 has a tapered shape in which the outer diameter and the inner diameter are reduced toward the distal end. Note that the inner layer 50 is preferably made of fluorine-based resin such as polytetrafluoroethylene having low sliding resistance. Further, the inner layer 50 may be partially or wholly formed in a multilayer structure.

The braid 52 corresponding to the first reinforcing body is disposed on the outside in the radial direction of the inner layer 50, and is wound along the outer peripheral surface of the inner layer 50. For this reason, the braid 52 corresponding to the first reinforcing body is reduced in diameter from the proximal end side toward the distal end side in the radial direction of the reduced diameter portion 60 of the inner layer 50. That is, the braid 52 corresponding to the first reinforcing body has a tapered shape that is reduced in diameter toward the distal end in the radial direction of the reduced diameter portion 60 of the inner layer 50. Note that the taper angle of the reduced diameter portion 60 and the taper angle of the braid 52 corresponding to the first reinforcing body are substantially the same. In other words, the inclination angle of the reduced diameter portion 60 with respect to the central axis of the catheter main body 30 and the inclination angle of the braid 52 corresponding to the first reinforcing body with respect to the central axis of the catheter main body 30 are substantially the same.

Further, the distal end of the braid 52 corresponding to the first reinforcing body is disposed in the distal tip 32 and is positioned on the proximal end side than the distal end of the inner layer 50. Note that in the present embodiment, the braid 52 corresponding to the first reinforcing body is arranged by knitting a plurality of strands. However, as the first reinforcing body, there may be arranged a coil formed by spirally winding a single strand or a coil formed by spirally winding a plurality of strands. Also, the braid 52 corresponding to the first reinforcing body is made of a material such as stainless steel, a superelastic alloy such as a Ni—Ti alloy, a piano wire, or a tungsten wire.

The reinforcing layer 54 is disposed so as to cover the outer periphery of the inner layer 50 and the braid 52 corresponding to the first reinforcing body. The reinforcing layer 54 includes an outer layer 62 and a coil 64 corresponding to the second reinforcing body. The outer layer 62 covers the outer periphery of the inner layer 50 and the braid 52 corresponding to the first reinforcing body, and the distal end of the outer layer 62 forms the distal end of the catheter main body 30. Further, the coil 64 corresponding to the second reinforcing body is disposed coaxially with the outer layer 62 in a state of being embedded in the outer layer 62. That is, the coil 64 corresponding to the second reinforcing body is disposed on the outside in the radial direction of the braid 52 corresponding to the first reinforcing body covered by the outer layer 62, and the outer layer 62 covers the inner layer 50, the braid 52 corresponding to the first reinforcing body, and the coil 64 corresponding to the second reinforcing body. Note that the distal tip of the coil 64 corresponding to the second reinforcing body extends to the vicinity of the distal tip of the outer layer 62.

In addition, the coil 64 corresponding to the second reinforcing body is reduced in diameter from the proximal end side toward the distal end side in the radial direction of the reduced diameter portion 60 of the inner layer 50, similarly to the braid 52 corresponding to the first reinforcing body. That is, the coil 64 corresponding to the second reinforcing body also has a tapered shape reduced in diameter toward the distal end side in the radial direction of the reduced diameter portion 60 of the inner layer 50, similarly to the braid 52 corresponding to the first reinforcing body. However, the taper angle of the coil 64 corresponding to the second reinforcing body is made smaller than the taper angle of the braid 52 corresponding to the first reinforcing body. In other words, the inclination angle of the coil 64 corresponding to the second reinforcing body is made smaller than the inclination angle of the braid 52 corresponding to the first reinforcing body. Thus, the coil 64 corresponding to the second reinforcing body is reduced in diameter more gently from the proximal end side toward the distal end side in the radial direction of the reduced diameter portion 60 of the inner layer 50, than the braid 52 corresponding to the first reinforcing body. Accordingly, the thickness of the outer layer 62 between the braid 52 corresponding to the first reinforcing body and the coil 64 corresponding to the second reinforcing body is increased from the proximal end side toward the distal end side in the radial direction of the reduced diameter portion 60.

Moreover, the outer peripheral surface of the outer layer 62 is also reduced in diameter from the proximal end side toward the distal end side in the radial direction of the reduced diameter portion 60 of the inner layer 50, and has a tapered shape. Then, the taper angle of the outer peripheral surface of the outer layer 62 is substantially same as the taper angle of the coil 64 corresponding to the second reinforcing body.

Note that in the present embodiment, the coil 64 is used as the second reinforcing body. However, the present disclosure is not limited thereto, and it is possible to use a braid in which a plurality of strands are knitted mutually. Moreover, the coil 64 corresponding to the second reinforcing body may be formed by spirally winding a single strand, or may be formed by spirally winding a plurality of strands. The second reinforcing body is made of a material such as stainless steel, a superelastic alloy such as a Ni—Ti alloy, a piano wire, or a tungsten wire. Moreover, the resin material forming the outer layer 62 includes, for example, polyamide, polyamide elastomer, polyester, or polyurethane. In this embodiment, a polyether block amide copolymer is used.

Moreover, the distal tip 32 has a multilayer structure, and includes the inner layer 50, the braid 52 corresponding to the first reinforcing body, and a distal outer layer 68 formed continuously from the outer layer 62 of the catheter main body 30 in this order from the radially inner side with respect to the central axis of the distal tip 32. The distal outer layer 68 is reduced in diameter toward the distal end side, and has a tapered shape.

Note that the resin material forming the distal outer layer 68 includes, for example, polyamide, polyamide elastomer, polyester, or polyurethane, similarly to the outer layer 62 of the catheter main body 30. Note that polyurethane is used for the distal outer layer 68 of this embodiment. In this manner, the main part of the distal tip 32 is made of polyurethane, whereby it is possible to prevent damages to the inner wall of the blood vessel. Further, in order to improve the visibility of the distal tip 32, the tip outer layer 68 preferably contains a radiopaque tungsten powder or the like.

As described above, in the catheter tube 22, as illustrated in FIG. 2, the thickness of the outer layer 62 positioned between the braid 52 corresponding to the first reinforcing body and the coil 64 corresponding to the second reinforcing body is increased from the proximal end side toward the distal end side in the radial direction of the reduced diameter portion 60. For this reason, it is possible to ensure the flexibility of the reduced diameter portion 60.

Specifically, in the catheter 10, the taper angle of the braid 52 corresponding to the first reinforcing body is intentionally made different from the taper angle of the coil 64 corresponding to the second reinforcing body in the radial direction of the reduced diameter portion 60, so that the taper angle of the coil 64 corresponding to the second reinforcing body is smaller than the taper angle of the braid 52 corresponding to the first reinforcing body. Accordingly, the thickness of the outer layer 62 between the braid 52 corresponding to the first reinforcing body and the reinforcing member 64 is increased from the proximal end side toward the distal end side in the radial direction of the reduced diameter portion 60. That is, the outer layer 62 between the braid 52 corresponding to the first reinforcing body and the reinforcing member 64 becomes thicker from the proximal end side toward the distal end side in the radial direction of the reduced diameter portion 60. For this reason, in the reduced diameter portion 60, when the guide wire inserted into the lumen 58 of the catheter 10 pushes from the proximal end side toward the distal end side, the thick outer layer 62 on the distal end side is preferably bent. This enhances the cushioning property and allows the outer layer 62 to function as a buffer.

Thereby, the flexibility of the reduced diameter portion 60 is ensured, and even if the guide wire comes into contact with the reduced diameter portion when the guide wire is inserted into the catheter 10, it is possible to prevent damages to the reduced diameter portion and deformation of the pre-shape of the guidewire.

Further, in the catheter 10, the coil 64 corresponding to the second reinforcing body has a tapered shape that is reduced in diameter toward the distal end side in the reduced diameter portion 60, so that the end on the distal end side of the catheter main body 30 has a tapered shape that is reduced in diameter toward the distal end side. Thereby, it is possible to preferably insert the catheter 10 into the blood vessel.

Second Embodiment

The following will describe a catheter according to the second embodiment. The parts same as in the catheter of the first embodiment will be represented with the same referential symbols in the drawings while the description thereof is simplified or omitted.

Figure 3:
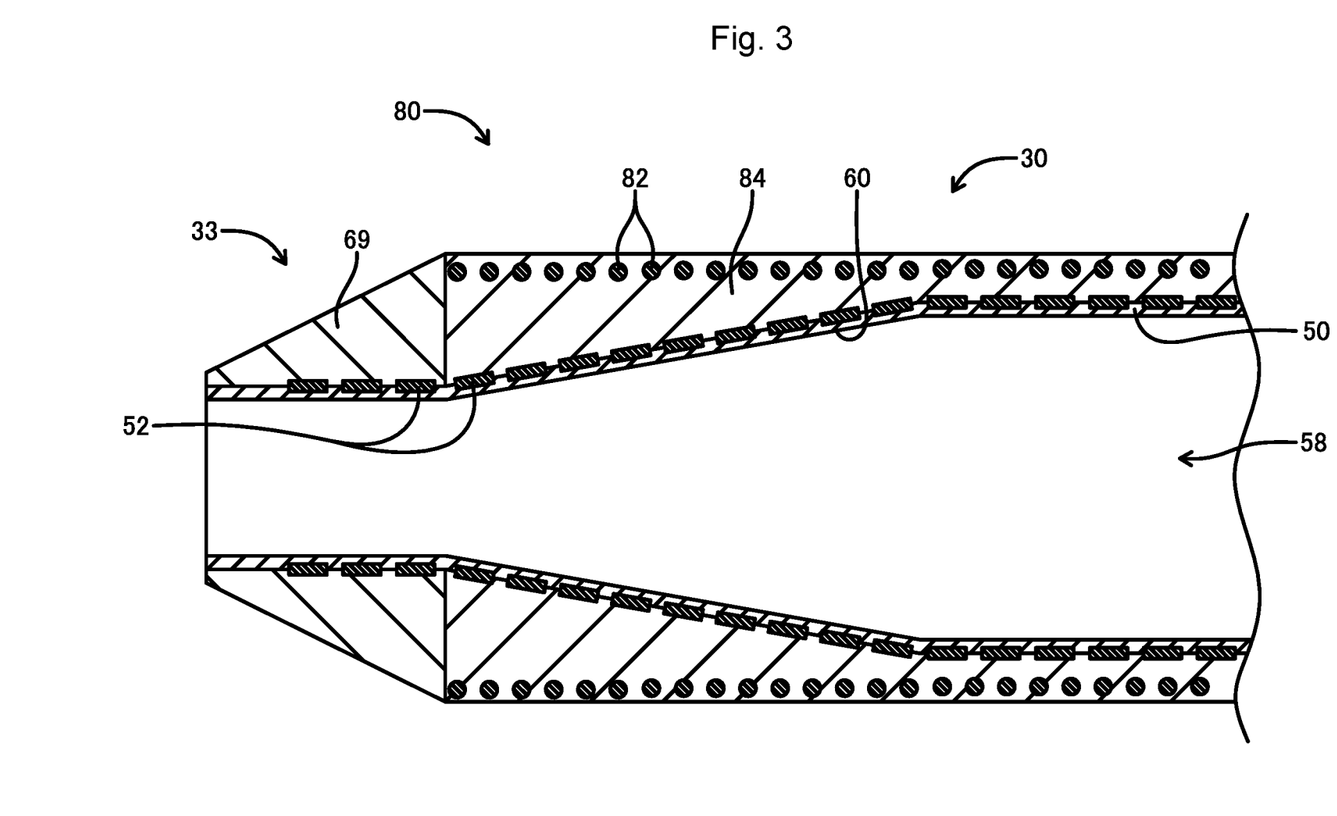
FIG. 3 is a partially enlarged sectional view of a catheter according to a second embodiment.

FIG. 3 is a partially enlarged sectional view of a catheter 80 according to the second embodiment. In FIG. 3, the catheter 80 is different from the catheter 10 of the first embodiment in that a coil 82 corresponding to the second reinforcing body is not reduced in diameter in the radial direction of the reduced diameter portion 60.

That is, in the catheter 10 of the first embodiment, as illustrated in FIG. 2, the coil 64 corresponding to the second reinforcing body is reduced in diameter more gently than the braid 52 corresponding to the first reinforcing body in the radial direction of the reduced diameter portion 60. Meanwhile, in the catheter 80 of the second embodiment, as illustrated in FIG. 3, the coil 82 corresponding to the second reinforcing body is not reduced in diameter in the radial direction of the reduced diameter portion 60.

In such a configuration, the thickness of an outer layer 84 between the braid 52 corresponding to the first reinforcement body and the coil 82 corresponding to the second reinforcement body is increased from the proximal end portion toward the distal end side in the radial direction of the reduced diameter portion 60, and is larger than the thickness of the outer layer 62 between the braid 52 corresponding to the first reinforcing body and the reinforcing member 64 in the first embodiment. For this reason, it is possible to more preferably ensure the flexibility of the reduced diameter portion 60.

Note that in the second embodiment, the braid 52 in which a plurality of strands are knitted mutually is disposed as the first reinforcing body, and the coil 82 is used as the second reinforcing body. However, the present disclosure is not limited thereto. Similarly to the first embodiment, there may be disposed, as the first reinforcing body, a coil in which a single strand is wound spirally or a coil in which a plurality of strands are wound spirally. Further, as the second reinforcing body, there may be used a braid in which a plurality of strands are knitted mutually.

Note that a distal tip 33 jointed to the distal end of the catheter main body 30 has a multilayer structure similarly to the distal tip 32 of the first embodiment, and includes the inner layer 50, the braid 52 corresponding to the first reinforcing body, and a distal outer layer 69 formed continuously from the outer layer 84 of the catheter main body 30 in this order from the radially inside with respect to the central axis of the distal tip 33.

Third Embodiment

The following will describe a catheter according to the third embodiment. The parts same as in the catheter of the first embodiment will be represented with the same referential symbols in the drawings while the description thereof is simplified or omitted.

Figure 4:
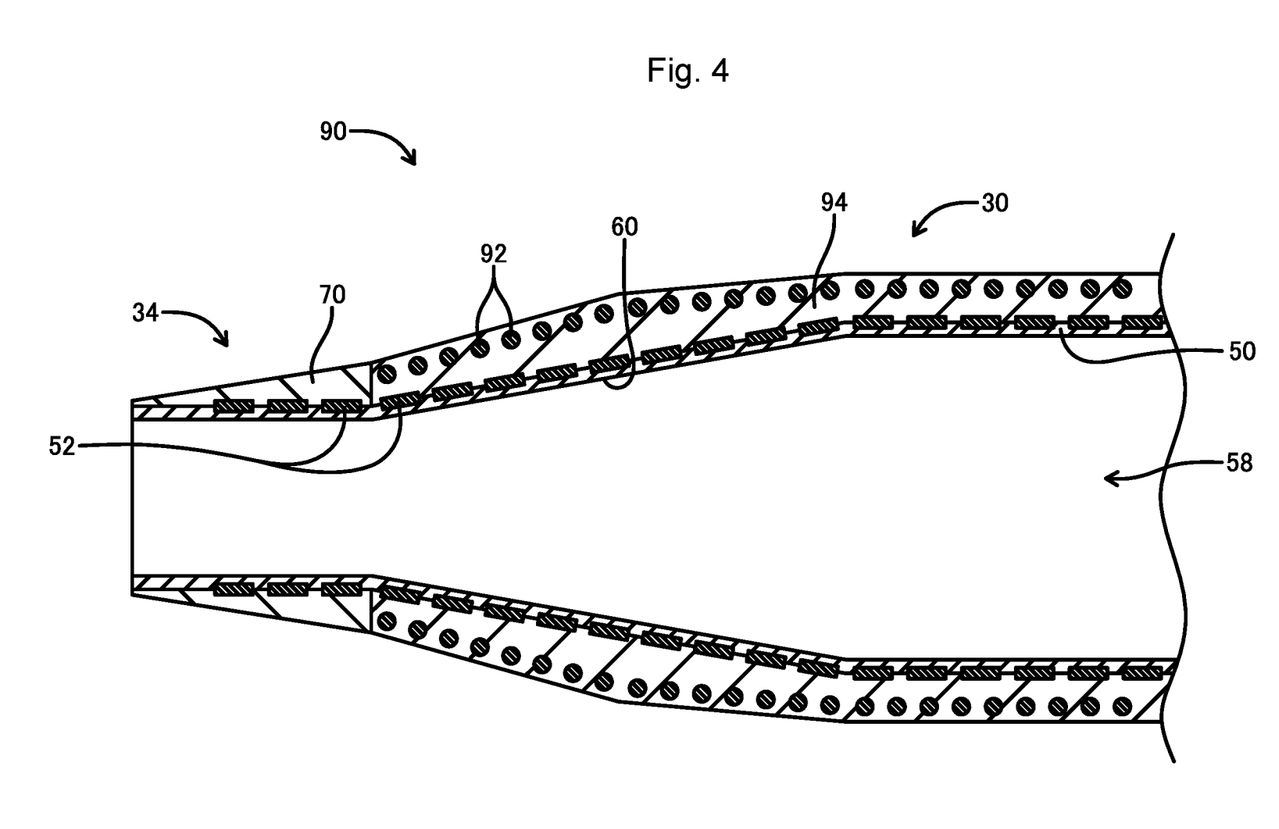
FIG. 4 is a partially enlarged sectional view of a catheter according to a third embodiment.

FIG. 4 is a partially enlarged sectional view of a catheter 90 according to the third embodiment. In FIG. 4, the catheter 90 is different from the catheter 10 of the first embodiment in that the thickness of an outer layer 94 between a coil 92 corresponding to the second reinforcing body and the braid 52 corresponding to the first reinforcing body is increased from the proximal end portion toward the distal end side in a partial area in the radial direction of the reduced diameter portion 60.

That is, in the catheter 10 of the first embodiment, as illustrated in FIG. 2, the coil 64 corresponding to the second reinforcing body is reduced in diameter more gently than the braid 52 corresponding to the first reinforcing body in the entire area in the radial direction of the reduced diameter portion 60. Accordingly, the thickness of the outer layer 62 between the coil 64 corresponding to the second reinforcing body and the braid 52 corresponding to the first reinforcing body is increased from the proximal end side toward the distal end side in the entire area in the radial direction of the reduced diameter portion 60. Meanwhile, in the catheter 90 of the third embodiment, as illustrated in FIG. 4, the coil 92 corresponding to the second reinforcement body is reduced in diameter more gently from the end on the proximal end side toward the distal end side than the braid 52 corresponding to the first reduced diameter portion, and then reduced in diameter more rapidly than the braid 52 corresponding to the first reinforcing body in the radial direction of the reduced diameter portion 60. That is, the taper angle of the coil 92 corresponding to the second reinforcing body from the end on the proximal end side to the center part is made smaller than the taper angle of the braid 52 corresponding to the first reinforcing body, while the taper angle of the coil 92 corresponding to the second reinforcing body from the center part to the end on the distal end side is made larger than the taper angle of the braid 52 corresponding to the first reinforcing body. Accordingly, the thickness of the outer layer 94 between the coil 92 corresponding to the second reinforcing body and the braid 52 corresponding to the first reinforcing body is increased from the proximal end portion toward the distal end side in an area from the end on the proximal end side to the center part in the radial direction of the reduced diameter portion 60.

Also in such a configuration, the thickness of the outer layer 94 between the coil 92 corresponding to the second reinforcing body and the braid 52 corresponding to the first reinforcing body is increased in the partial area in the radial direction of the reduced diameter portion 60. Thus, it is possible to ensure the flexibility of the reduced diameter portion 60. Further, the taper angle of the reinforcing member 92 increases toward the distal end side. Therefore, it is possible to further reduce the diameter of the end on the distal end side of the catheter 90, and preferably insert the catheter 90 into the blood vessel.

Note that in the third embodiment, the braid 52 in which a plurality of strands are knitted mutually is disposed as the first reinforcing body, and the coil 92 is used as the second reinforcing body. However, the present disclosure is not limited thereto. Similarly to the first embodiment, there may be disposed, as the first reinforcing body, a coil in which a single strand is wound spirally or a coil in which a plurality of strands are wound spirally. Further, as the second reinforcing body, there may be used a braid in which a plurality of strands are knitted mutually.

Note that a distal tip 34 jointed to the distal end of the catheter main body 30 has a multilayer structure similarly to the distal tip 32 of the first embodiment, and includes the inner layer 50, the braid 52 corresponding to the first reinforcing body, and a distal outer layer 70 formed continuously from the outer layer 94 of the catheter main body 30 in this order from the radially inside with respect to the central axis of the distal tip 34.

Note that the catheter 10 of the above-described embodiment is an example of the catheter of the present disclosure. The inner layer 50 is an example of the inner layer of the present disclosure. The braid 52 is an example of the first reinforcing body of the present disclosure. The reduced diameter portion 60 is an example of the reduced diameter portion of the present disclosure. The outer layer 62 is an example of the outer layer of the present disclosure. The coil 64 is an example of the second reinforcing body of the present disclosure. The catheter 80 is an example of the catheter of the present disclosure. The coil 82 is an example of the second reinforcing body of the present disclosure. The outer layer 84 is an example of the outer layer of the present disclosure. The catheter 90 is an example of the catheter of the present disclosure. The coil 92 is an example of the second reinforcing body of the present disclosure. The outer layer 94 is an example of the outer layer of the present disclosure.

Note that the present disclosure is not limited to the above-described embodiments, and it is possible to implement the disclosure in various aspects in which various changes and modifications are applied on the basis of knowledge of those skilled in the art. Specifically, for example, in the above-described embodiments, the distal end of the reduced diameter portion 60 reaches the distal end of the catheter main body 30. However, the distal end of the reduced diameter portion 60 may not reach the distal end of the catheter main body 30. That is, a reduced diameter portion may be formed between the end on the distal end side and the end on the proximal end side of the catheter main body 30. Also in such a case, the same effects as those described in the embodiments are exerted.

Moreover, in the above-described embodiments, one reduced diameter portion 60 is formed in the catheter 10, 80, 90. However, a plurality of reduced diameter portions 60 may be formed. That is, it is possible to employ a structure in which the lumen 58 of the catheter 10, 80, 90 is reduced in diameter in multiple stages. In such a configuration, in the radial direction of at least one of the plurality of reduced diameter portions 60, the thickness of the outer layer between the first reinforcing body and the second reinforcing body may increase from the proximal end side toward the distal end side. Also in such a case, the same effects as those described in the embodiments are exerted.

Moreover, in the above-described embodiments, two reinforcing bodies of the first reinforcing body and the second reinforcing body are arranged in the catheter. However, three or more reinforcing bodies may be arranged. In such a configuration, the thickness of the outer layer between at least two reinforcing bodies facing in the radial direction among the three or more reinforcing bodies may be increased from the proximal end side toward the distal end side. Also in such a case, the same effects as those described in the embodiments are exerted. However, in the aspect in which the thickness of the outer layer between the reinforcing body positioned on the innermost side in the radial direction among the three or more reinforcing bodies and the reinforcing body facing such a reinforcing body is increased, the largest effects are exerted.

Note that in the above-described embodiments, the outer layer 62, 84, and 94 is formed as a single layer. However, the present disclosure is not limited thereto. For example, in the case where the outer layer 62, 84, and 94 is formed in two layers (outer lower layer and outer upper layer), an outer lower layer may be formed between the first reinforcing body and the second reinforcing body, and an outer upper layer may be formed so as to cover the outer periphery of the second reinforcing body. In such a case, the thickness of the outer lower layer positioned between the first reinforcing body and the second reinforcing body may be increased at least in a partial area from the proximal end side toward the distal end side in the radial direction of the reduced diameter portion.

REFERENCE SIGNS LIST 10, 80, 90 catheter
20 operation part
30 catheter main body
32, 33, 34 distal tip
50 inner layer
52 first reinforcing body (braid)

60 reduced diameter portion
62, 84, 94 outer layer
64, 82, 92 second reinforcing body (coil)
68, 69, 70 distal outer layer

The invention claimed is:

1. A catheter, comprising:
a tubular inner layer;
a first reinforcing body that is wound around an outside in a radial direction of the inner layer;
a second reinforcing body that is wound around the outside in the radial direction of the first reinforcing body; and
an outer layer that covers the inner layer, the first reinforcing body, and the second reinforcing body, wherein
the inner layer has a reduced diameter portion that is reduced in diameter from a proximal end side of the catheter toward a distal end side of the catheter on an inner peripheral surface of the inner layer, and
a thickness of the outer layer between the first reinforcing body and the second reinforcing body is increased, at least partially from the proximal end side toward the distal end side, in the radial direction of the reduced diameter portion.

2. The catheter according to claim 1, wherein the first reinforcing body is reduced in diameter, from the proximal end side toward the distal end side, in the radial direction of the reduced diameter portion.

3. The catheter according to claim 2, wherein the second reinforcing body is reduced in diameter more gently than the first reinforcing body, at least partially from the proximal end side toward the distal end side, in the radial direction of the reduced diameter portion.

4. The catheter according to claim 3, wherein the thickness of the outer layer between the first reinforcing body and the second reinforcing body is increased in the radial direction of the at least partially of the second reinforcing body reduced in diameter more gently than the first reinforcing body.

5. The catheter according to claim 2, wherein the second reinforcing body is not reduced in diameter at least partially from the proximal end side toward the distal end side in the radial direction of the reduced diameter portion.

6. The catheter according to claim 5, wherein the thickness of the outer layer between the first reinforcing body and the second reinforcing body is increased in the radial direction of the at least partially of the second reinforcing body not reduced in diameter.

7. The catheter according to claim 1, wherein
the first reinforcing body is reduced in diameter, from the proximal end side toward the distal end side, in the radial direction of the reduced diameter portion,
the second reinforcing body is reduced in diameter, from the proximal end side toward the distal end side, in the radial direction of a first part of the reduced diameter portion,
the second reinforcing body is reduced in diameter, from the proximal end side toward the distal end side, in the radial direction of a second part of the reduced diameter portion, the second part of the reduced diameter portion being closer to the proximal end side than the first part of the reduced diameter portion, and
the second reinforcing body is reduced in diameter more gently in the second part of the reduced diameter portion than in the first part of the reduced diameter portion.

8. The catheter according to claim 7, wherein
the thickness of the outer layer between the first reinforcing body and the second reinforcing body is increased from the proximal end side toward the distal end side, in the radial direction of the reduced diameter portion, in the second part of the reduced diameter portion, and
the thickness of the outer layer between the first reinforcing body and the second reinforcing body is decreased from the proximal end side toward the distal end side, in the radial direction of the reduced diameter portion, in the first part of the reduced diameter portion.

9. The catheter according to claim 1, wherein the tubular inner layer is made of fluorine-based resin.

10. The catheter according to claim 1, wherein the first reinforcing body is either: a braid arranged by knitting a plurality of strands, a coil formed by spirally winding a single strand, or a coil formed by spirally winding a plurality of strands.

11. The catheter according to claim 10, wherein the first reinforcing body is made of at least one of: stainless steel, a Ni—Ti alloy, a piano wire, and a tungsten wire.

12. The catheter according to claim 1, wherein the second reinforcing body is a coil formed by spirally winding a single strand, or a coil formed by spirally winding a plurality of strands.

13. The catheter according to claim 12, wherein the second reinforcing body is made of at least one of: stainless steel, a Ni—Ti alloy, a piano wire, and a tungsten wire.

14. The catheter according to claim 1, wherein the outer layer includes at least one of: polyamide, polyamide elastomer, polyester, and polyurethane.

* * * * *